(12) United States Patent
Jackson et al.

(10) Patent No.: US 9,889,195 B2
(45) Date of Patent: Feb. 13, 2018

(54) IMMUNOGENIC COMPOSITION AND USES THEREOF

(71) Applicant: THE UNIVERSITY OF MELBOURNE, Parkville (AU)

(72) Inventors: David Charles Jackson, North Balwyn (AU); Weiguang Zeng, Kensington (AU); Brendon Yew Loong Chua, Heidelberg Heights (AU)

(73) Assignee: INNAVAC PTY LTD (AU)

( * ) Notice: Subject to any disclaimer, the term of this patent is extended or adjusted under 35 U.S.C. 154(b) by 0 days.

(21) Appl. No.: 14/602,778

(22) Filed: Jan. 22, 2015

(65) Prior Publication Data

US 2015/0150966 A1    Jun. 4, 2015

Related U.S. Application Data

(63) Continuation of application No. 13/268,069, filed on Oct. 7, 2011, now abandoned, which is a continuation of application No. PCT/AU2009/000469, filed on Apr. 16, 2009, and a continuation-in-part of application No. PCT/AU2009/000446, filed on Apr. 9, 2009.

(51) Int. Cl.

| | |
|---|---|
| *A61K 39/39* | (2006.01) |
| *A61K 31/23* | (2006.01) |
| *A61K 38/03* | (2006.01) |
| *A61K 38/38* | (2006.01) |
| *A61K 45/06* | (2006.01) |
| *C07K 2/00* | (2006.01) |
| *C07K 14/77* | (2006.01) |
| *A61K 39/00* | (2006.01) |

(52) U.S. Cl.
CPC ............ *A61K 39/39* (2013.01); *A61K 31/23* (2013.01); *A61K 38/03* (2013.01); *A61K 38/38* (2013.01); *A61K 45/06* (2013.01); *C07K 2/00* (2013.01); *C07K 14/77* (2013.01); *A61K 2039/55516* (2013.01); *A61K 2039/6018* (2013.01)

(58) Field of Classification Search
None
See application file for complete search history.

(56) References Cited

U.S. PATENT DOCUMENTS

| | | | |
|---|---|---|---|
| 8,986,700 B2* | 3/2015 | Jackson | A61K 39/145 424/184.1 |
| 9,089,508 B2* | 7/2015 | Jackson | A61K 39/00 |
| 2004/0191270 A1 | 9/2004 | Drane et al. | |
| 2007/0066534 A1 | 3/2007 | Jackson et al. | |
| 2008/0069831 A1 | 3/2008 | Duke et al. | |
| 2008/0069832 A1 | 3/2008 | Chomez et al. | |
| 2010/0310595 A1 | 12/2010 | Jackson et al. | |
| 2011/0280899 A1 | 11/2011 | Jackson et al. | |

FOREIGN PATENT DOCUMENTS

| | | |
|---|---|---|
| EP | 1550458 | 7/2005 |
| EP | 1 666 056 A1 | 6/2006 |
| WO | WO 2001/037869 | 5/2001 |
| WO | WO 2004/014956 A1 | 2/2004 |
| WO | WO 2004/014957 A1 | 2/2004 |
| WO | WO 2005/112991 | 12/2005 |
| WO | WO 2006/069262 | 6/2006 |
| WO | WO 2006/084319 | 8/2006 |
| WO | WO 2006/091591 | 8/2006 |
| WO | WO 2008/085549 | 7/2008 |
| WO | WO 2009/046498 | 4/2009 |
| WO | WO 2009/155332 | 12/2009 |
| WO | WO 2010/028246 | 3/2010 |
| WO | WO 2010/093436 | 8/2010 |
| WO | WO 2010/111485 | 9/2010 |
| WO | WO 2011/080259 | 7/2011 |

OTHER PUBLICATIONS

Baz, 2008, Vaccine, 26, 2570-2579 (cited in the prosecution of the parent application).*
Metzger, 1991, Int. J. Peptide Protein Res., 37, 46-57 (cited in the prosecution of the parent application).*
Website: http://medical-dictionary.thefreedictionary.com/admixture, 3 apges, Aug. 26, 2016.*
Rothbard, The EMBO Journal vol. 7 No. 1 pp. 93-100, 1988.*
Ghielmetti, M. et al. "Synthetic bacterial lipopeptide analogs facilitate naïve CD4+ T cell differentiation and enhance antigen-specific HLA-II-restricted responses" *Eur. J. Immunol.*, 2005, 35:2434-2442.
Meng, G. et al. "Cellular recognition of tri-/di-palmitoylated peptides is independent from a domain encompassing the N-terminal seven leucine-rich repeat (LRR)/LRR-like motifs of TLR2" *J. Biol. Chem.*, 2003, 278(41):39822-39829.
Andrä, J. et al. "Enhancement of endotoxin neutralization by coupling of a C12-alkyl chain to a lactoferricin-derived peptide" *Biochem. J.*, Jan. 1, 2005, 385(1):135-143.
Farley, M.M. et al. "Lipopolysaccharide Structure Determines Ionic and Hydrophobic Binding of a Cationic Antimicrobial Neutrophil Granule Protein" *Infection and Immunity*, Jun. 1988, 56(6):1589-1592.
Pina, D.G. et al. "Shiga toxin B-subunit sequential binding to its natural receptor in lipid membranes" *Biochimica et Biophysica Acta*, 2007, 1768:628-636.
Metzger, J. et al. "Synthesis of novel immunologically active tripalmitoyl-S-glycerylcysteinyl lipopeptides as useful intermediates for immunogen preparations" *Int. J. Peptide Protein Res.*, 1991, 37:46-57.
Baz, A. et al. "Branched and linear lipopeptide vaccines have different effects on primary CD4+ and CD8+ T-cell activation but induce similar tumor-protective memory CD8+ T-cell responses" *Vaccine*, 2008, 26:2570-2579.

(Continued)

*Primary Examiner* — Satyanarayana R Gudibande
(74) *Attorney, Agent, or Firm* — Saliwanchik, Lloyd & Eisenschenk (57) ABSTRACT

The present invention provides an immunogenic composition comprising an antigen and a dendritic cell targeting component. A charged group is covalently attached to a dendritic cell ligand and is electrostatically associated with the dendritic cell targeting component.

3 Claims, 5 Drawing Sheets

(56) References Cited

OTHER PUBLICATIONS

Tansey, W. et al. "Synthesis and characterization of branched poly(L-glutamic acid) as a biodegradable drug carrier" *J. Controlled Release*, 2004, 94:39-51.
Zeng, W. et al. "Highly immunogenic and totally synthetic lipopeptides as self-adjuvanting immunocontraceptive vaccines" *J. Immunol.*, 2002, 169:4905-4912.
Ismaili, J. et al. "Monophosphoryl lipid A activates both human dendritic cells and T cells" *J. Immunol.*, 2002, 168:926-932.
Raffai, R. et al. "Molecular characterization of two monoclonal antibodies specific for the LDL receptor-binding site of human apolipoprotein E" *J. Lipid Res.*, 1995, 36:1905-1918.
Raffai, R. et al. "Binding of an antibody mimetic of the human low density lipoprotein receptor to apolipoprotein E is governed through electrostatic forces" *J. Biol. Chem.*, 2000, 275(10):7109-7116.
Amigorena, S. "Fcγ receptors and cross-presentation in dendritic cells" *J. Exp. Med.*, 2002, 195(1):F1-F3.
Alexopoulou et al. "Recognition of double-stranded RNA and activation of NF-kappaB by Toll-like receptor 3" *Nature*, Oct. 18, 2001, 413(6857):732-8.
Asea et al. "Novel signal transduction pathway utilized by extracellular HSP70: role of toll-like receptor (TLR) 2 and TLR4" *J Biol Chem*, Apr. 26, 2002, 277(17):15028-34.
Brown and Gordon "Immune recognition. A new receptor for beta-glucans" *Nature*, Sep. 6, 2001, 413(6851):36-7.
Bulut et al. "Chlamydial heat shock protein 60 activates macrophages and endothelial cells through Toll-like receptor 4 and MD2 in a MyD88-dependent pathway" *J Immunol*, 2002, 168(3):1435-40.
Chow et al. "Toll-like receptor-4 mediates lipopolysaccharide-induced signal transduction" *J Biol Chem*, Apr. 16, 1999, 274(16):10689-92.
Chua et al. "Dendritic cell acquisition of epitope cargo mediated by simple cationic peptide structures" *Peptides*, 2008, 29:881-890.
Chua et al. "Soluble Proteins Induce Strong CD8+ T Cell and Antibody Responses through Electrostatic Association with Simple Cationic or Anionic Lipopeptides That Target TLR2" *The Journal of Immunology*, 2011, 187:1692-1701.
Chua et al. "Enhancing immunogenicity of HCV DNA vaccines by targeted delivery to dendritic cells" *Journal of Hepatology*, 2008, 48:S236, abstract No. 634.
Duggan et al. "Synergistic Interactions of TLR2/6 and TLR9 Induce a High Level of Resistance to Lung Infection in Mice" *The Journal of Immunology*, 2011, 186:5916-5926.
Engering et al. "The mannose receptor functions as a high capacity and broad specificity antigen receptor in human dendritic cells" *Eur J Immunol*, Sep. 1997, 27(9):2417-25.
Feinberg et al. "Structural basis for selective recognition of oligosaccharides by DC-SIGN and DC-SIGNR" *Science*, Dec. 7, 2001, 294(5549):2163-6.
Frison et al. "Oligolysine-based oligosaccharide clusters: selective recognition and endocytosis by the mannose receptor and dendritic cell-specific intercellular adhesion molecule 3 (ICAM-3)-grabbing nonintegrin" *J Biol Chem*, Jun. 27, 2003, 278(26):23922-9.
Hayashi et al. "The innate immune response to bacterial flagellin is mediated by Toll-like receptor 5" *Nature*, Apr. 26, 2001, 410(6832):1099-103.
Heil et al. "Species-specific recognition of single-stranded RNA via toll-like receptor 7 and 8" *Science*, Mar. 5, 2004, 303(5663):1526-9.
Hemmi et al. "Small anti-viral compounds activate immune cells via the TLR7 MyD88-dependent signaling pathway" *Nat Immunol*, Feb. 2002, 3(2):196-200.
Hemmi et al. "A Toll-like receptor recognizes bacterial DNA" *Nature*, Dec. 7, 2000, 408(6813):740-5.
Jackson et al. "A totally synthetic vaccine of generic structure that targets Toll-like receptor 2 on dendritic cells and promotes antibody or cytotoxic T cell responses" *Proceedings of the National Academy of Sciences*, 2004, 101:15440-15445.
Kery et al. "Ligand recognition by purified human mannose receptor" *Arch Biochem Biophys*, Oct. 1992 298(1):49-55.
Morr et al. "Differential recognition of structural details of bacterial lipopeptides by toll-like receptors" *Eur J Immunol*, Dec. 2002, 32(12):3337-47.
Okusawa et al. "Relationship between structures and biological activities of mycoplasmal diacylated lipopeptides and their recognition by toll-like receptors 2 and 6" *Infect Immun*, Mar. 2004, 72(3): 1657-65.
Ozinsky et al. "The repertoire for pattern recognition of pathogens by the innate immune system is defined by cooperation between toll-like receptors" *Proc Natl Acad Sci USA*, Dec. 5, 2000, 97(25):13766-71.
Poltorak et al. "Defective LPS signaling in C3H/HeJ and C57BL/10ScCr mice: mutations in Tlr4 gene" *Science*, Dec. 11, 1998, 282(5396):2085-8.
Schwandner et al. "Peptidoglycan- and lipoteichoic acid-induced cell activation is mediated by toll-like receptor 2" *J Biol Chem*, Jun. 18, 1999, 274(25):17406-9.
Stambach and Taylor "Characterization of carbohydrate recognition by langerin, a C-type lectin of Langerhans cells" *Glycobiology*, May 2003, 13(5):401-10.
Takeuchi et al. "Cutting edge: preferentially the R-stereoisomer of the mycoplasmal lipopeptide macrophage-activating lipopeptide-2 activates immune cells through a toll-like receptor 2- and MyD88-dependent signaling pathway" *J Immunol*, Jan. 15, 2000, 164(2):554-7.
Takeuchi et al. "Cutting edge: role of Toll-like receptor 1 in mediating immune response to microbial lipoproteins" *J Immunol*, Jul. 2002, 169(1):10-14.
Tighe et al. "Conjugation of protein to immunostimulatory DNA results in a rapid, long-lasting and potent induction of cell-mediated and humoral immunity" *European Journal of Immunology*, 2000, 30:1939-1947.
Zeng et al. "Synthesis of a New Template with a Built-in Adjuvant and Its Use in Constructing Peptide Vaccine Candidates Through Polyoxime Chemistry" *Journal of Peptide Science*, 1996, 2:66-72.
Alphs, HH et al., "Protection against heterologous human papillomavirus challenge by a synthetic lipopeptide vaccine containing a broadly cross-neutralizing epitope of L2" *Proceedings of the National Academy of Science*, 2008, 105(15):5850-5855.
Archer, K.A. et al., "MyD88-Dependent Responses Involving Toll-Like Receptor 2 Are Important for Protection and Clearance of *Legionella pneumophila* in a Mouse Model of Legionnaires' Disease," *Infection and Immunity*, 2006, 74(6):3325-3333.
Azuma, M. et al. "The peptide sequence of diacyl lipopeptides determines dendritic cell TLR2-mediated NK activation" *PLoS One*, 2010, 5(9):e12550.
Basto, A.P. et al., "Targeting TLR2 for Vaccine Development," *Journal of Immunology Research*, 2014, Article No. 619410, pp. 1-22.
Belz, G.T., et al., "A Previously Unrecognized H-2D$^b$-Restricted Peptide Prominent in the Primary Influenza A Virus-Specific CD8$^+$ T-Cell Response Is Much Less Apparent following Secondary Challenge," *Journal of Virology*, Apr. 2000, vol. 74, No. 8, pp. 3486-3493.
Bodmer, H.C., et al., "Enhanced Recognition of a Modified Peptide Antigen by Cytotoxic T Cells Specific for Influenza Nucleoprotein," *Cell*, Jan. 29, 1988, vol. 52, pp. 253-258.
Cleret, A., et al., "Lung Dendritic Cells Rapidly Mediate Anthrax Spore Entry through the Pulmonary Route," *Journal of Immunology*, 2007, vol. 178, pp. 7994-8001.
Cluff, C.W. et al., "Toll-Like Receptor 4 Agonists Stimulate Innate Resistance to Infectious Challenge," *Infection and Immunity*, 2005, 73(5):3044-3052.
Firat, H., et al., "H-2 class I knockout, HLA-A2.1-transgenic mice: a versatile animal model for preclinical evaluation of antitumor immunotherapeutic strategies," *Eur. J. Immunol.*, 1999, vol. 29, pp. 3112-3121.
Fuse, E. et al. "Role of Toll-like receptor 2 in recognition of *Legionella pneumophila* in a murine pneumonia model" *J. Med. Microbiol.*, 2007, 56:305-312.

(56) References Cited

OTHER PUBLICATIONS

Gianfrani, C., et al., "Human Memory CTL Response Specific for Influenza A Virus is Broad and Multispecific," *Human Immunology*, 2000, vol. 61, pp. 438-452.

Gonzalez-Juarrero, M., et al., "Dynamics of Macrophage Cell Populations During Murine Pulmonary Tuberculosis," *Journal of Immunology*, 2003, vol. 171, pp. 3128-3135.

Gotch, F., et al., "Cytotoxic T lymphocytes recognize a fragment of influenza virus matrix protein in association with HLA-A2," *Nature*, Apr. 30, 1987, vol. 326, pp. 881-882.

Heuking, S. et al. "Stimulation of human macrophages (THP-1) using Toll-like receptor-2 (TLR-2) agonist decorated nanocarriers" *J. Drug Targeting*, 2009, 17(8):662-670.

Hoffman, P. et al. "Induction of tumor cytotoxicity in murine bone marrow-derived macrophages by two synthetic lipopeptide analogues" *Biol. Chem. Hoppe-Seyler*, 1989, 370:575-582.

Jameson, J., et al., "Human CD8+ and CD4+ T Lymphocyte Memory to Influenza A Viruses of Swine and Avian Species," *Journal of Immunology*, 1999, vol. 162, pp. 7578-7583.

Landsman, L., et al., "Lung Macrophages Serve as Obligatory Intermediate between Blood Monocytes and Alveolar Macrophages," *Journal of Immunology*, 2007, vol. 179, pp. 3488-3494.

Licalsi, C. et al., "Dry powder inhalation as a potential delivery method for vaccines," *Vaccine*, 1999, 17(13-14):1796-1803.

Martinez, J. et al. "Direct TLR2 signaling is critical for NK cell activation and function in response to vaccinia viral infection" *PLoS Pathogens*, 2010, 6(3):e1000811.

Mühlradt, P. et al. "Structure and specific activity of macrophage-stimulating lipopeptides from *Mycoplasma hyorhinis*" *Infection and Immunity*, 1998, 66(10):4804-4810.

Pascolo, S., et al., "HLA-A2.1-restricted Education and Cytolytic Activity of CD8+ T Lymphocytes from β2 Microglobulin (β2m) HLA-A2.1 Monochain Transgenic H-2D$^b$ β2m Double Knockout Mice," *J. Exp. Med.*, Jun. 16, 1997, vol. 185, No. 12, pp. 2043-2051.

Reppe, K. et al., "Immunostimulation with Macrophage-Activating Lipopeptide-2 Increased Survival in Murine Pneumonia," *Am. J. Respir. Cell. Mol. Biol.*, 2009, 40(4):474-481.

Rose, WA et al., "FSL-1, a bacterial-derived toll-like receptor 2/6 agonist, enhances resistance to experimental HSV-2 infection" *Virology Journal*, 2009, 6:195-205.

Seifert, R. et al. "Activation of superoxide formation and lysozyme release in human neutrophils by the synthetic lipopeptide $Pam_3Cys$-Ser-$(Lys)_4$" *Biochem. J.*, 1990, 267:795-802.

Sherman, L.A., et al., "Extracellular Processing of Peptide Antigens That Bind Class I Major Histocompatibility Molecules," *J. Exp. Med.*, May 1992, vol. 175, pp. 1221-1226.

Tannock, G.A., et al., "Relative Immunogenicity of the Cold-Adapted Influenza Virus Ann Arbor/6/60 (A/AA/6/60-ca), Recombinants of A/AA/6/60-ca, and Parental Strains with Similar Surface Antigens," *Infection and Immunity*, Feb. 1984, vol. 43, No. 2, pp. 457-462.

TLR-2, Wikipedia, the free encyclopedia, undated, pp. 1-6.

Voss, S et al., "The activity of lipopeptide TLR2 agonists critically depends on the presence of solubilizers" *European Journal of Immunology*, 2007, 37:3489-3498.

Wallace, M.E., et al., "The Cytotoxic T-Cell Response to Herpes Simplex Virus Type 1 Infection of C57BL/6 Mice Is Almost Entirely Directed against a Single Immunodominant Determinant," *Journal of Virology*, Sep. 1999, vol. 73, No. 9, pp. 7619-7626.

Zeng, W., et al., "Characterisation of the antibody response to a totally synthetic immunocontraceptive peptide vaccine based on LHRH," *Vaccine*, 2005, vol. 23, pp. 4427-4435.

Deliyannis, G. et al. "Intranasal lipopeptide primes lung-resident memory CD8+ T cells for long-term pulmonary protection against influenza," *European Journal of Immunology*, 2006, vol. 36, pp. 770-780.

Lau, Y.F. et al. "Lipid-containing mimetics of natural triggers of innate immunity as CTL-inducing influenza vaccines," *International Immunology*, 2006, vol. 18, No. 12, pp. 1801-1813.

Palma, C. et al. "The Toll-like Receptor 2/6 Ligand MALP-2 Reduces the Viability of *Mycobacterium tuberculosis* in Murine Macrophages," *The Open Microbiology Journal*, 2009, vol. 3, pp. 47-52.

\* cited by examiner

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial
<220> FEATURE:
<223> OTHER INFORMATION: OVA258-265 peptide

<400> SEQUENCE: 1

Ser Ile Ile Asn Phe Glu Lys Leu
1               5
```

IMMUNOGENIC COMPOSITION AND USES THEREOF

CROSS-REFERENCE TO RELATED APPLICATIONS

The present application is a continuation of U.S. patent application Ser. No. 13/268,069, filed Oct. 7, 2011, which is a continuation-in-part of International Patent Application No. PCT/AU2009/000446, filed Apr. 9, 2009, and is a continuation of International Patent Application No. PCT/AU2009/000469, filed Apr. 16, 2009, the disclosures of which are incorporated by reference herein in their entirety, including any figures, tables, or drawings.

BACKGROUND OF INVENTION

There is an ever increasing interest in the development of compositions which can be used to raise an immune response in humans and other animals in particular to protect against disease. In generating an immune response it is necessary for the antigen to encounter dendritic cells. Dendritic cells are immune cells and form part of the mammalian immune system. Their main function is to process antigen material and present it on the surface to other cells of the immune system, thus functioning as antigen-presenting cells.

The targeting of antigens to dendritic cells has been contemplated previously and lipopeptides which include lipids which Toll-like receptors on dendritic cells have been shown to elicit strong immune response (WO 2004/014956 & WO 2004/014957, the disclosures of which are incorporated herein be reference)

For any peptide to be able to induce an effective antibody response it must contain particular sequences of amino acids known as epitopes that are recognised by the immune system. In particular, for antibody responses, epitopes need to be recognised by specific immunoglobulin (Ig) receptors present on the surface of B lymphocytes. It is these cells which ultimately differentiate into plasma cells capable of producing antibody specific for that epitope. In addition to these B cell epitopes, the immunogen must also contain epitopes that are presented by antigen presenting cells (APC) to specific receptors present on helper T lymphocytes, the cells which are necessary to provide the signals required for the B cells to differentiate into antibody producing cells.

In the case of viral infections and in many cases of cancer, antibody is of limited benefit in recovery and the immune system responds with cytotoxic T cells (CTL) which are able to kill the virus-infected or cancer cell. Like helper T cells, CTL are first activated by interaction with APC bearing their specific peptide epitope presented on the surface, this time in association with MHC class I rather than class II molecules. Once activated the CTL can engage a target cell bearing the same peptide/class I complex and cause its lysis. It is also becoming apparent that helper T cells play a role in this process; before the APC is capable of activating the CTL it must first receive signals from the helper T cell to upregulate the expression of the necessary costimulatory molecules.

Helper T cell epitopes are bound by molecules present on the surface of APCs that are coded by class II genes of the major histocompatibility complex (MHC). The complex of the class II molecule and peptide epitope is then recognised by specific T-cell receptors (TCR) on the surface of T helper lymphocytes. In this way the T cell, presented with an antigenic epitope in the context of an MHC molecule, can be activated and provide the necessary signals for the B lymphocyte to differentiate.

In general then, an immunogen must contain epitopes capable of being recognised by helper T cells in addition to the epitopes that will be recognised by B cells or by cytotoxic T cells. It should be realised that these types of epitopes may be very different. For B cell epitopes, conformation is important as the B cell receptor binds directly to the native immunogen. In contrast, epitopes recognised by T cells are not dependent on conformational integrity of the epitope and consist of short sequences of approximately nine amino acids for CTL and slightly longer sequences, with less restriction on length, for helper T cells. The only requirements for these epitopes are that they can be accommodated in the binding cleft of the class I or class II molecule respectively and that the complex is then able to engage the T-cell receptor. The class II molecule's binding site is open at both ends allowing a much greater variation in the length of the peptides bound (Brown, J. H., T. S. Jardetzky, J. C. Gorga, L. J. Stern, R. G. Urban, J. L. Strominger and D. C. Wiley. 1993. Three-dimensional structure of the human class II histocompatibility antigen HLA-DR1. Nature 364: 33) although epitopes as short as 8 amino acid residues have been reported (Fahrer, A. M., Geysen, H. M., White, D. O., Jackson, D. C. and Brown, L. E. Analysis of the requirements for class II-restricted T-cell recognition of a single determinant reveals considerable diversity in the T-cell response and degeneracy of peptide binding to I-ED J. Immunol. 1995. 155: 2849-2857).

BRIEF SUMMARY

The present inventors have developed immunogenic compositions comprising an antigen and a dendritic cell targeting component in which the antigen is electrostatically associated with the dendritic cell targeting component.

In a first aspect the present invention provides an immunogenic composition comprising an antigen and a dendritic cell targeting component, wherein the antigen comprises a negatively charged region and wherein the dendritic cell targeting component comprises a positively charged group covalently attached to a dendritic cell ligand and wherein the negatively charged region of antigen is electrostatically associated with the dendritic cell targeting component.

In a second aspect the present invention provides an immunogenic composition comprising an antigen and a dendritic cell targeting component, wherein the antigen comprises a positively charged region and wherein the dendritic cell targeting component comprises a negatively charged group covalently attached to a dendritic cell ligand and wherein the positively charged region of antigen is electrostatically associated with the dendritic cell targeting component.

In a third aspect the present invention provides a method of raising an immune response in a subject, the method comprising administering to a subject an immunogenic composition of the first or second aspect of the present invention.

BRIEF DESCRIPTION OF DRAWINGS

In the following, OVA=ovalbumin; HEL=hen egg white lysozyme; $R_4(S_2Pam_2Cys)$=construct shown at 1 in FIG. 5; $E_4(S_2Pam_2Cys)$=construct shown at 2 in FIG. 5; CFA=complete Freund's adjuvant.

FIG. 1. Antibody and cell-mediated responses elicited by vaccination with $R_4(S_2Pam_2Cys\text{-}OVA)$ complexes. (A) Groups of BALB/c mice were inoculated subcutaneously with 25 µg of OVA alone, OVA emulsified in CFA or OVA that had been mixed with an equimolar or a 5-fold molar excess of $R_4(S_2Pam_2Cys)$. Animals received a second and similar dose of antigen 26 days later. Sera were obtained from blood taken 27 days after the primary (○) and 13 days following the secondary (●) inoculation of antigen. Antibody levels were determined by ELISA and individual antibody titres presented with the mean value represented by the horizontal bar. (B) Mice were inoculated a third time on day 50 and spleens obtained 7 days later. Intracellular cytokine staining was performing on splenocytes to detect the presence of SIINFEKL-specific IFN-γ producing $CD8^+$ T cells. Data are presented as the mean and standard deviation of triplicate samples.

FIG. 2. OVA and HEL-specific antibody responses elicited by vaccination with cationic and anion lipopeptide-protein complexes. BALB/c mice were inoculated subcutaneously with 25 µg of HEL (A) or OVA (B) alone, emulsified in CFA or with an equal amount of $R_4(S_2Pam_2Cys)$ or $E_4(S_2Pam_2Cys)$ that had been mixed with the antigen. Mice were bled 28 days after the primary (○) inoculation, boosted on day 32 and bled again on day 46 (●). Antibody levels were then determined by ELISA. Individual animal titres are presented with the mean value represented by the horizontal bar.

FIG. 3. Sedimentation of ovalbumin-lipopeptide complexes. Increasing amounts of the branched $R_4(S_2Pam_2Cys)$ or linear $Pam_2Cys\text{-}SK_4$ lipopeptide were mixed with 1 nmole of ovalbumin (OVA) in a total volume of 100 µl PBS in a flat flat-bottom 96-well plate. The turbidity of the solution was then measured by determining the optical density of the solution at 450 nm.

DETAILED DISCLOSURE

The present inventors have found that a charged moiety covalently attached to a dendritic cell targeting group associate with an antigen electrostatically to form an immunogenic complex which can be used to raise an immune response.

Accordingly the present invention provides an immunogenic composition comprising an antigen and a dendritic cell targeting component, wherein the antigen comprises a negatively charged region and wherein the dendritic cell targeting component comprises a positively charged group covalently attached to a dendritic cell ligand and wherein the negatively charged region of antigen is electrostatically associated with the dendritic cell targeting component.

In this aspect of the invention it is important that the antigen includes a negatively charged region or domain which can electrostatically interact with the charged targeting component. It is however not essential that the antigen has an overall negative charge, although this is preferred. It is also possible to increase the negative charge of the antigen by adding negatively charged groups. For example with a polypeptide antigen a chain of aspartic acid or glutamic acid residues could be added to the polypeptide.

It is preferred that the positively charged group comprises at least one positively charged amino acid. It is also preferred that the positively charged group is a branched or linear peptide, preferably branched. In various embodiments the peptide will include at least one arginine, histidine, ornithine or lysine residue or combinations thereof. It is preferred that the peptide comprises at least four arginine residues and/or at least four lysine residues. It is particularly preferred that the positively charged group comprises a branched peptide comprising at least 4 arginine residues.

In a second aspect the present invention provides an immunogenic composition comprising an antigen and a dendritic cell targeting component, wherein the antigen comprises a positively charged region and wherein the dendritic cell targeting component comprises a negatively charged group covalently attached to a dendritic cell ligand and wherein the positively charged region of antigen is electrostatically associated with the dendritic cell targeting component.

In this aspect of the invention it is important that the antigen includes a positively charged region or domain which can electrostatically interact with the charged targeting component. It is however not essential that the antigen has an overall positive charge, although this is preferred. It is also possible to increase the positive charge of the antigen by adding positively charged groups. For example with a polypeptide antigen a chain of lysine, arginine or histidine residues could be added to the polypeptide.

It is preferred that the negatively charged group comprises at least one negatively charged amino acids. It is also preferred that the negatively charged group is a branched or linear peptide, preferably branched. In various embodiments the peptide will include at least one aspartic acid or glutamic acid residue or combinations thereof. It is preferred that the peptide comprises at least four aspartic acid residues and/or at least four glutamic acid residues. It is particularly preferred that the positively charged group comprises a branched peptide comprising at least 4 glutamic acid residues.

In a preferred embodiment of the present invention the antigen is not a nucleic acid. It is also preferred that the antigen is associated with the dendritic cell targeting component by electrostatic interaction only.

A range of dendritic cell ligands which may be used in the present invention are set out in Table 1. It is preferred however that the dendritic cell ligand is a TLR ligand. The TLR ligand may comprise a lipid or a peptidoglycan or a lipoprotein or a lipopolysaccharide. In particular, the TLR ligand may comprise palmitoyl, myristoyl, stearoyl, lauroyl, octanoyl, or decanoyl. Preferably the TLR ligand is selected from the group consisting of: Pam2Cys, Pam3Cys, Ste2Cys, Lau2Cys, and Oct2Cys.

In certain embodiments the TLR ligand binds TLR-2, which may be associated TLR-1, or TLR-6.

In a third aspect the present invention provides a method of raising an immune response in a subject, the method comprising administering to a subject an immunogenic composition according to the first or second aspects of the present invention.

octanoyl, or decanoyl. Preferred groups include $Pam_2Cys$, $Pam_3Cys$, $Ste_2Cys$, $Lau_2Cys$, and $Oct_2Cys$.

Reference to "immune response" as used herein means a reference to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

TABLE 1

Pathogen Associated Molecular Pattern (PAMP) receptors expressed by DCs

| Family | Receptor | Ligand | References |
|---|---|---|---|
| Toll-like receptors | TLR-1 | triacylated bacterial lipids (TLR-1 & 2) | (Takeuchi 2002) |
| | TLR-2 | peptidoglycan, yeast zymosan, bacterial lipoproteins | (Schwandner 1999, Ozinsky 2000, Takeuchi 2000) |
| | TLR-3 | | |
| | TLR-4 | double stranded RNA | (Alexopoulou 2001) |
| | TLR-5 | LPS, hsp60 & hsp70 | (Poltorak 1998, Chow 1999, Asea 2002, Bulut 2002) |
| | TLR-6 | flagellin | |
| | TLR-7 | diacylated bacterial lipids (TLR-2 & 6) | (Hayashi 2001) |
| | TLR-8 | imidazoquinoline compounds | (Morr 2002, Okusawa 2004) |
| | TLR-9 | single stranded RNA | (Hemmi 2002) |
| | TLR-10 | CpG DNA | (Heil 2004) |
| | | yet to be discovered | (Hemmi 2000) |
| C-type lectins | Mannose Receptor | Mannose-, fucose-, glucose-, GlcNAc-containing carbohydrates | (Kery 1992, Engering 1997) |
| | Langerin, DC-SIGN | Mannose-, fucose-containing carbohydrates | (Feinberg 2001, Frison 2003, Stambach 2003) |
| | Dectin-1 | β-glucans | |
| | DEC-205 | yet to be discovered | (Brown 2001) |

Abbreviations:
CpG, cytosine phosphate guanine;
Fc, fragment crystallisable;
GlcNAc, N-acetyl glucosamine;
hsp, heat shock protein;
LPS, lipopolysaccharide;
RNA, ribonucleic acid An exemplary dendritic cell targeting compound of the present invention is the lipopeptide "$Pam_2Cys$". One of skill in the art would understand that the term "lipopeptide" means any composition of matter comprising one or more lipid moieties and one or more amino acid sequences that are conjugated. "$Pam_2Cys$" (also known as dipalmitoyl-S-glyceryl-cysteine or S-[2,3bis(palmitoyloxy)propyl]cysteine has been synthesised (Metzger, J. W. et al. 1995. J Pept Sci 1: 184) and corresponds to the lipid moiety of MALP-2, a macrophage-activating lipopeptide isolated from *Mycoplasma fermentans* (Sacht, G. et al. 1998. Eur J Immunol 28:4207; Muhiradt, P. F. et al. 1998. Infect Immun 66: 4804; Muhiradt, P. F. et al. 1997. J Exp Med 185: 1951). $Pam_2Cys$ is known to be a ligand of TLR-2.

$Pam_2Cys$ has the structure of Formula (I):

Other lipid moieties which may be used to target cell surface TLRs include palmitoyl, myristoyl, stearoyl, lauroyl, Throughout this specification the word "comprise", or variations such as "comprises" or "comprising", will be understood to imply the inclusion of a stated step or element or integer or group of steps or elements or integers but not the exclusion of any other step or element or integer or group of elements or integers.

All the references cited in this application are specifically incorporated by reference herein.

Reference to any prior art in this specification is not, and should not be taken as, an acknowledgment or any form of suggestion that this prior art forms part of the common general knowledge in Australia.

It would be appreciated that the person of skill in the art may introduce any combination of positively charged group and TLR ligand as befits the desired application.

The present invention will now be described further with reference to the following non-limiting examples:

Methods and Materials

Synthesis of Lipopeptides

Figure 5:
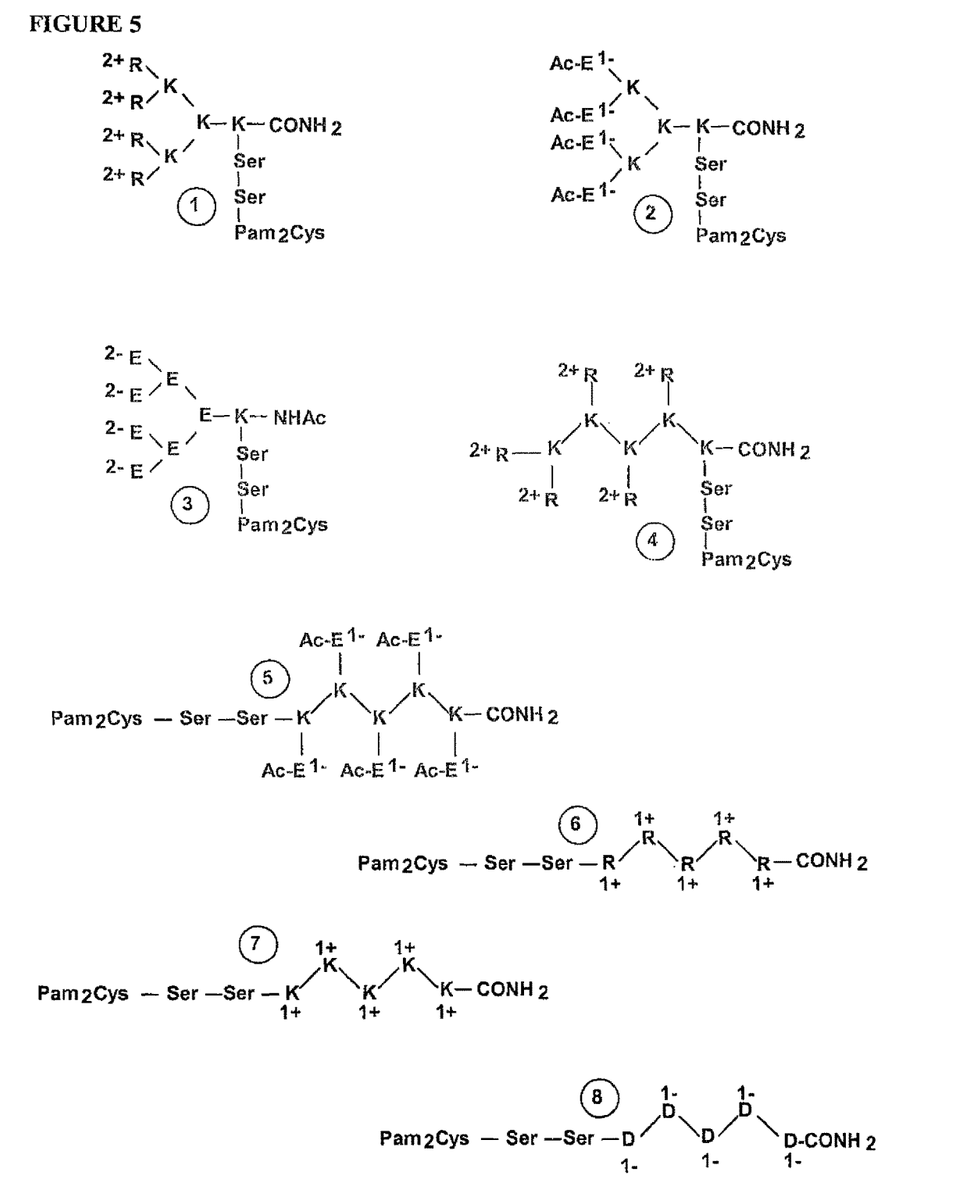
FIG. 5 Schematic representations of some examples of branched (structures 1-5) and linear (structures 6-8) immunogenic compositions comprising of positively charged (Arginine, R; Lysine, K) or negatively charged (Aspartic acid, D; Glutamic acid, E) amino acids in terminal positions such that their respective electrostatic charges are displayed to the environment. Each immunogenic composition also contains dipalmitoyl-S-glyceryl cysteine (Pam2Cys) which is a ligand for Toll-Like Receptor 2. Two serine residues (Ser) are also incorporated. In the case of construct 2 the peptide structure was assembled in the direction N→C, all other structures shown in the figure were assembled C→N. Positive and negative electrostatic charges are shown as 2−, 2+, 1−, 1+ etc. depending on the size of charge. Ac=acetyl group used to suppress the positive charge of alpha amino groups in the case of N-terminally situated Glutamic acid.

The synthesis of branched and linear lipopeptides was carried out on PEG-S RAM resin (Rapp Polymere, Tübingen, Germany; substitution factor 0.27 mmol/g). For the synthesis of the branched lipopeptides $R_4(S_2Pam_2Cys)$(construct 1) and $E_4(S_2Pam_2Cys)$(construct 2; see schematic representations), Fmoc-lysine(Mtt)-OH (Novabiochem, Laufelfingen, Switzerland) was first coupled to the resin at a 4-fold excess with equimolar amounts of O-benzotriazole-N,N,N',N'-tetramethyl-uronium-hexafluorophosphate (HBTU; Novabiochem, Darmstadt, Germany), 1-hydroxybenzotriazole (HOBt) and a 1.5-fold molar excess of diisopropylethylamine (DIPEA; Sigma, Castle Hill, Australia). Acylation was carried out for 40 minutes. The Fmoc protective group on the -amino was then removed and Fmoc-lysine(Fmoc)-OH was coupled such that following removal of these Fmoc groups, two primary amino groups were exposed to act as branching points. Subsequent coupling of another round of Fmoc-lysine(Fmoc)-OH at an 8-fold excess yielded four branch points to which four arginine (R) or glutamic acid (E) residues were coupled at a 16-fold excess.

For the lipidation of branched constructs, the amino groups of the N-terminal arginine acid residues were protected using a 10-fold molar excess of di-tert-butyl dicarbonate (Fluka Chemika, Switzerland) in the presence of DIPEA. The Boc protective groups were removed upon successful lipidation and cleavage. The glutamic acid residues are acetylated with acetic anhydride to block the a-amino groups and also suppress the positive charges of the a-amino groups of the final product. The Mtt protective group present on the ε-amino group of the C-terminal lysine was then removed and two serines were coupled. The $Pam_2Cys$ lipid moiety was then coupled according to Zeng et al (Zeng 2003) to generate branched $R_4(S_2Pam_2Cys)$ or branched $E_4(S_2Pam_2Cys)$.

In the case of the linear lipopeptide $Pam_2Cys$-$SK_4$, Fmoc-lysine(Boc)-OH and Fmoc-Serine(tBu)-OH were used to synthesise the linear peptide followed by coupling of the $Pam_2Cys$ lipid moiety.

Following assembly, lipopeptides were cleaved from the solid phase support with 88% TFA, 5% phenol, 2% TIPS, 5% water for 3 hours at room temperature and were analysed by reversed phase high-pressure liquid chromatography (RP-HPLC) using a Vydac C4 column (4.6×300 mm) installed in a Waters HPLC system. The chromatogram was developed at a flow rate of 1 ml/min using 0.1% TFA in $H_2O$ and 0.1% TFA in acetonitrile as the limit solvent. Products were purified if necessary and presented as a single major peak on analytical RP-HPLC and had the expected mass when analysed using an Agilent series 1100 ion trap mass spectrometer.

Immunization Protocols

Groups of five female, 8-12 week old BALB/c mice were inoculated subcutaneously in the base of the tail on day 0 and again on day 28 unless otherwise stated with either 25 μg of ovalbumin (OVA; Sigma Aldrich, USA) or hen egg lysozyme (HEL; Sigma Aldrich, USA) in saline or emulsified in CFA, or mixed with different amounts of $R_4(S_2Pam_2Cys)$ or $E_4(S_2Pam_2Cys)$ in saline. Sera were prepared from blood taken at approximately 4 weeks following the primary inoculation and 2 weeks following the secondary inoculation unless otherwise stated.

Enzyme-Linked Immunosorbent Assay (ELISA)

Flat bottom well polyvinyl plates (Thermo, USA) were coated with either OVA or HEL (5 μg/ml) in PBS containing w/v 0.1% sodium azide (Chem Supply, Australia) for 18-20 hours at room temperature in a humidified atmosphere. The antigen was removed and PBS containing 10 mg/ml bovine serum albumin ($BSA_{10}$PBS) was added for 1 hour before washing with PBS containing v/v 0.05% Tween-20 (Sigma Aldrich, Milwaukee, USA)(PBST). Serial dilutions of sera obtained from immunised mice were added to wells and incubated overnight at room temperature. After washing with PBST, bound antibody was detected using horseradish peroxidase-conjugated rabbit anti-mouse IgG antibodies (Dako, Glostrup, Denmark) in conjunction with enzyme substrate (0.2 mM 2,2'-azino-bis 3-ethylbenzthiazoline-sulfonic acid [Sigma Aldrich, Milwaukee, USA] in 50 mM citric acid [M&B, England] containing 0.004% hydrogen peroxide [Ajax Chemicals, Australia]). Colour development induced by the enzyme-substrate reaction was allowed to proceed for 15 minutes and was stopped by the addition of 50 mM sodium fluoride (BDH Chemicals, Australia). A Labsystems Multiscan Multisoft microplate reader (Pathtech Diagnostics, Australia) was used to determine the absorbance readings at 405 nm (with wavelength correction at 450 nm). The titers of antibody are expressed as the reciprocal of the highest dilution of serum required to achieve an optical density of 0.2.

Detection of IFN-γ Production by Intracellular Cytokine Staining

For the detection of specific $CD8^+$ T cell-mediated cytokine production, mice were administered with a third dose of OVA (25 μg) in saline or emulsified in CFA, or mixed with different amounts of $R_4(S_2Pam_2Cys)$. Seven days later spleens were obtained from inoculated mice and pressed through a metal sieve to obtain single cell suspensions. Splenocytes ($1\times10^6$) were then cultured with syngeneic irradiated (2200 rad, $^{60}Co$ source) naïve splenocytes ($5\times10^5$) with or without the $OVA_{258-265}$ peptide SIINFEKL (SEQ ID NO:1) (2 μg/ml) in the presence of recombinant IL-2 (10 U/ml; Roche, Mannheim, Germany). Brefeldin A (1 μg/ml) in the form of BD GolgiPlug from the Cytofix/Cytoperm Plus Kit (Becton Dickinson, USA) was also included in this culture. After 6 hours, lymphocytes were washed with FACs wash and stained with a PerCP-conjugated rat anti-mouse CD8 antibody (Clone 53-6.7; Becton Dickinson, USA) for 30 minutes at 4° C. Fixation and permeabilization was then performed for 20 minutes at 4° C. using Cytofix/Cytoperm solution (Cytofix/Cytoperm Plus Kit, Becton Dickinson, USA) according to the manufacturer's instructions. Cells were washed once with the kit-supplied Perm/Wash solution and stained with a FITC-conjugated rat anti-mouse IFN-γ antibody (Clone XMG1.2; Becton Dickinson, USA) for 30 minutes at 4° C. before analysis by flow cytometry. Data analysis was performed using FlowJo software (Treestar Inc, USA). Live viable cells were gated based on their forward and side scattering properties and a total of $1\times10^5$ $CD8^+$ cells counted.

Sedimentation of OVA-Lipopeptide Complexes

OVA (1 nmole) was mixed with increasing amounts of the branched $R_4(S_2Pam_2Cys)$ or linear $Pam_2Cys$-$SK_4$ lipopeptide in a total volume of 100 μl PBS in a flat-bottom 96-well plate. The turbidity of solution in each well was then determined by measuring its optical density at 450 nm on a Labsystems Multiscan Multisoft microplate reader.

Solutions containing either 100 nmoles of $R_4(S_2Pam_2Cys)$, 1 nmole of OVA or a mixture of $R_4(S_2Pam_2Cys)$ and OVA were also centrifuged ($1.2\times10^5$ G) and HPLC analysis performed on supernatants. Sedimented material from the mixture containing both the lipopeptide and OVA was also dissolved in a solution of 50% acetonitrile in water and then analysed by HPLC. In all samples, the identity of the peak corresponding to the lipopeptide was verified by mass spectrometry and that of OVA based on its retention time in the solution containing OVA alone.

All patents, patent applications, provisional applications, and publications referred to or cited herein, supra or infra, are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Introduction

Protein antigens, particularly recombinant proteins, are often not immunogenic and formulation with adjuvant is necessary to enhance their immunogenicity although concerns about adjuvant toxicity and their mechanism of action need to be resolved before they can be licensed for use in humans. Therefore the development of novel systems that can facilitate the delivery of protein antigens by directly targeting and concurrently activating antigen-presenting cells, such as the dendritic cell, could prove to be advantageous.

In this example, we describe the use of a charged and branched lipopeptide structure that can electrostatically bind protein antigens and deliver them to dendritic cells. The charge of the lipopeptide is mediated by the presence of four N-terminal arginine ($R_4$) or glutamic acid residues ($E_4$) imparting either an overall positive or negatively charge respectively to the delivery module. Hence $R_4$ can be used to bind negatively charged proteins and $E_4$ used for those that are positively charged. The incorporation of the TLR-2 targeting lipid moiety, $Pam_2Cys$, to the cationic ($R_4$ ($S_2Pam_2Cys$)) or anionic version ($E_4(S_2Pam_2Cys)$) of the branched lipopeptide ensures targeted delivery of bound protein to dendritic cells.

Results

The lipopeptide $R_4(S_2Pam_2Cys)$ has an overall charge of +8 due to the presence of four N-terminal arginine residues (each arginine having a +2 charge). To determine whether $R_4(S_2Pam_2Cys)$ can enhance protein immunogenicity through electrostatic interaction, ovalbumin (OVA), which has an overall negative charge of 11, was used as a model protein antigen.

Figure 1:
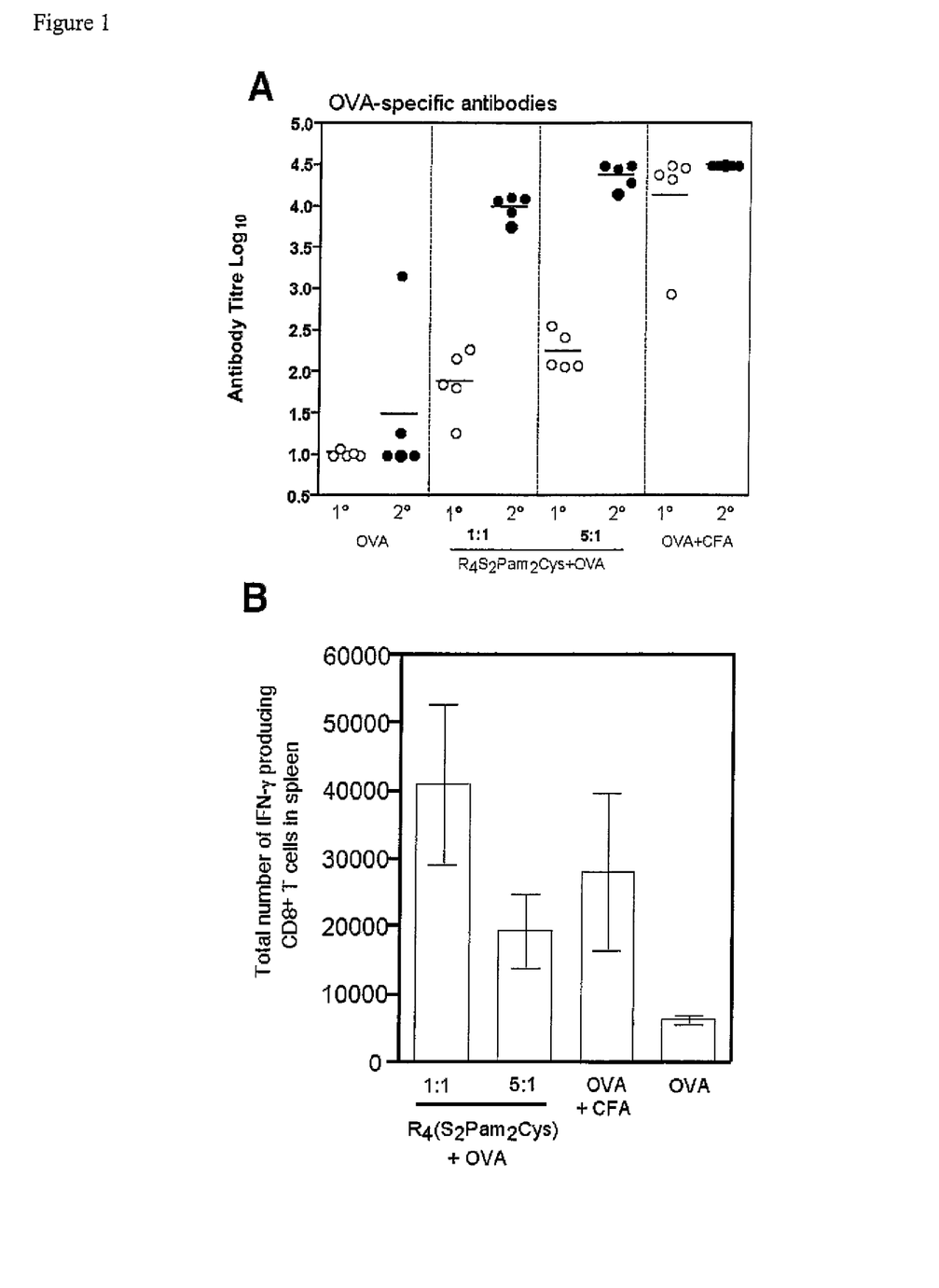

Vaccination with OVA pre-incubated with an equimolar or a 5-fold molar excess of $R_4(S_2Pam_2Cys)$ elicited significantly higher titres of anti-OVA antibodies in the primary and secondary response than did vaccination with OVA alone (FIG. 1A) indicating that association of the cationic lipopeptide with the protein can enhance its immunogenicity. The level of antibody elicited appears to be proportional to the amount of $R_4(S_2Pam_2Cys)$ used because a 5-fold excess of $R_4(S_2Pam_2Cys)$ resulted in higher antibody levels compared to those achieved when an equal amount $R_4(S_2Pam_2Cys)$ was used. Although the antibody levels in the primary response of mice in these groups were less than those obtained when mice were inoculated with OVA emulsified in complete Freund's adjuvant (CFA), the antibody levels obtained following a second dose of antigen in $R_4(S_2Pam_2Cys)$ were almost as high as those induced by FCA.

Cell-mediated responses were also analysed following vaccination with $R_4(S_2Pam_2Cys)$+OVA. The secretion of the pro-inflammatory cytokine, interferon-γ (IFN-γ) by $CD8^+$ T cells was measured as an indication of T cell activation. Vaccination with $R_4(S_2Pam_2Cys)$+OVA induced significantly more specific IFN-γ producing $CD8^+$ T cells in the spleen of inoculated mice than did inoculation with OVA alone and similar levels of IFN-γ producing $CD8^+$ T cells were elicited with $R_4(S_2Pam_2Cys)$ and CFA (FIG. 1B). In contrast to the antibody results where an increase in the amount of $R_4(S_2Pam_2Cys)$ used was associated with a higher antibody response, the opposite appears to be the case for cell-mediated responses; higher cytokine-secreting T cells were detected when an equimolar amount of $R_4(S_2Pam_2Cys)$ was used in comparison to when 5-fold excess was used. This observation suggests that by altering the ratio of $R_4(S_2Pam_2Cys)$ to protein antigen, it may be possible to select the appropriate (cellular vs humoral) type of immune response required for the clearance of a particular pathogen.

Figure 2:
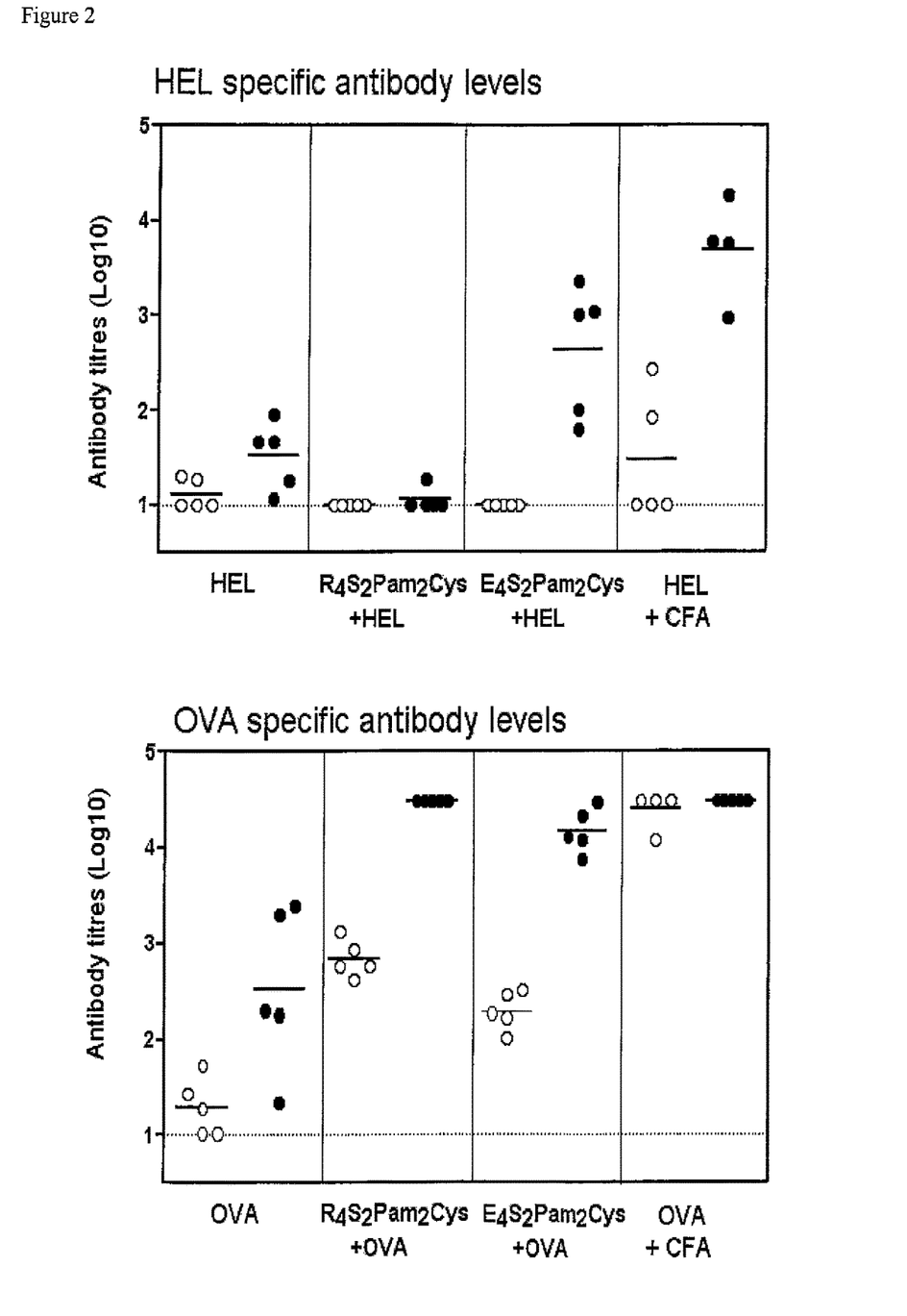

In order to determine if the electrostatic interaction between a negatively charged lipopeptide and a positively charged antigen can also provide the same immunogenic enhancement, the lipopeptide $E_4(S_2Pam_2Cys)$ (which has an overall charge of +4 due to the presence of four N-terminal glutamic acid residues) was incubated with hen egg lysozyme (HEL) which has an overall charge of +8. Inoculation of mice with these complexes resulted in higher antibody titres than those that were achieved with HEL alone indicating that the strategy of using Pam2Cys imbued with an electric charge opposite to the antigen with which it is administered can also be applied to accommodate protein antigens of the opposite charge (FIG. 2A).

It was also found that inoculation of mice with $R_4(S_2Pam_2Cys)$ and HEL, both of which have positive charges, did not result in the production of antibody indicating that the enhancement is charge specific. It remains to be seen however, whether the unexpected antibody results seen with E4($S_2Pam_2Cys$) and the negatively charged OVA are due to the $E_4(S_2Pam_2Cys)$ binding to positively charged patches present on OVA.

Discussion

The findings indicate that branched positively or negatively charged lipopeptides can be used to enhance the immunogenicity of oppositely charged proteins. This is especially highlighted through the use of $R_4(S_2Pam_2Cys)$, which although capable of inducing OVA-specific responses, is unable to augment HEL-specific responses. Considering the positive charge of this lipopeptide and those of the proteins examined, the effects observed are possibly due to electrostatic interactions, or lack of therein, between the Pam2Cys moiety and the antigen. Further investigations to confirm this hypothesis can be achieved through chromatographic methods of analysis and additional in vivo studies using similarly or oppositely charged protein antigens as well as the inclusion of a branched lipopeptide that has a neutral charge.

The results of these experiments also suggest that the type of immune response that can be induced i.e. humoral or cellular may depend on the ratio of charged lipopeptide and protein used. This could be a particularly significant finding because the successful clearance of particular pathogens can depend on the type of immune response that is elicited The lipopeptides that we describe here may therefore provide a means to tailor the desired immune response against the particular antigen according to the disease.

Example 2

Figure 3:
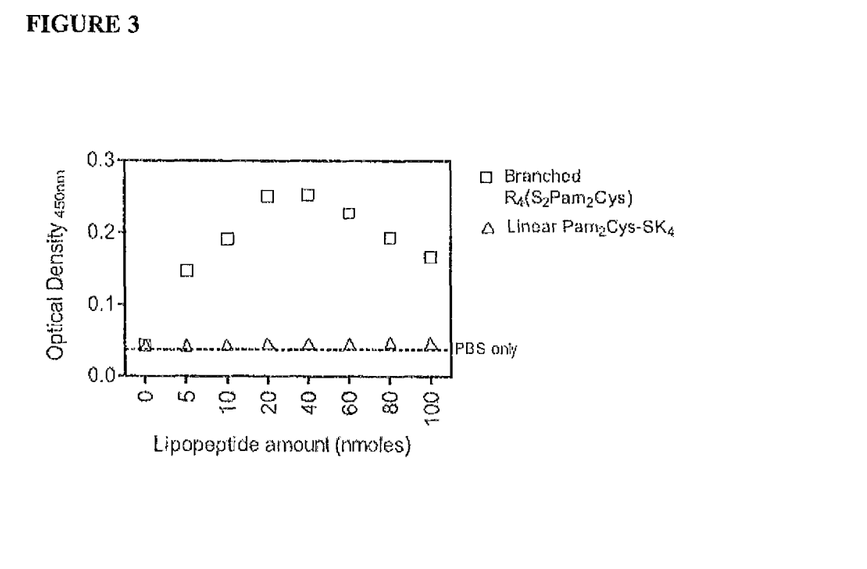

In order to measure the ability of the branched $R_4(S_2Pam_2Cys)$ and the linear $Pam_2Cys$-$SK_4$ lipopeptide to form a complex with the model antigen ovalbumin (OVA), the light absorbances of solutions containing increasing amounts of each lipopeptide and OVA were determined by measuring the optical density at 450 nm (FIG. 3). The ability of each lipopeptide to allow complex formation with OVA would therefore indicate an association between the two compounds.

It was found that the addition of 5 nmoles of branched $R_4(S_2Pam_2Cys)$ to a solution containing 1 nmole of OVA resulted in the formation of complexes which appeared as a turbid or opalescent solution. Increasing the amount of branched lipopeptide resulted in an increase in optical density readings with the highest achieved when 20 to 40 nmoles of lipopeptide was used. In contrast, very little increase in optical density was observed when the linear Pam2Cys-SK4 lipopeptide was added at all concentrations investigated indicating that branched $R_4(S_2Pam_2Cys)$ is superior to the linear lipopeptide at binding to the antigen.

To confirm the binding of $R_4(S_2Pam_2Cys)$ to OVA, solutions containing either of these compounds individually or a mixture of both were centrifuged to sediment any complex. HPLC analysis was then performed on the supernatant and on the sedimented material.

Figure 4:
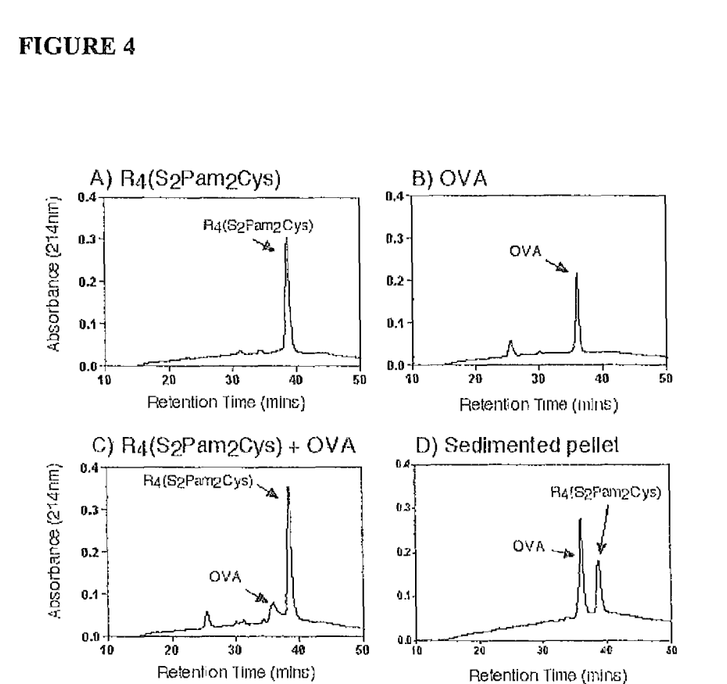
FIG. 4. HPLC analysis of ovalbumin-$R_4(S_2Pam_2Cys)$ lipopeptide solution. HPLC analysis was performed on supernatants of solutions containing either (A) 100 nmoles of branched $R_4(S_2Pam_2Cys)$ lipopeptide, (B) 1 nmole of ovalbumin (OVA) or (C) a mixture of $R_4(S_2Pam_2Cys)$ lipopeptide and ovalbumin in a total volume of 100 µl PBS following centrifugation ($1.2\times10^5$G). (D) Sedimented material from the mixture containing both the lipopeptide and OVA was dissolved in a solution of 50% acetonitrile in water and then analysed by HPLC. In all samples containing $R_4(S_2Pam_2Cys)$, the identity of the peak corresponding to the lipopeptide was verified by mass spectrometry.

In the supernatant of solutions containing either OVA or $R_4(S_2Pam_2Cys)$ (FIG. 4A), the resulting chromatograms revealed major peaks corresponding to each individual compound in solution. After mixing both compounds, a dramatic decrease in the size of the peak corresponding to OVA in solution was obvious suggesting that the protein had been sedimented out of solution as a result of association with the $R_4(S_2Pam_2Cys)$ lipopeptide. This was confirmed in the HPLC analysis of the reconstituted material (FIG. 4B) which revealed the presence of two major peaks corresponding to both OVA and lipopeptide confirming the sedimented material is a complex of lipopeptide and protein.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Alexopoulou L, Holt A C, Medzhitov R, Flavell R A. Recognition of double-stranded RNA and activation of NF-kappaB by Toll-like receptor 3. Nature 2001 Oct. 18; 413(6857):732-8.
Asea A, Rehli M, Kabingu E, Boch J A, Bare O, Auron P E, et al. Novel signal transduction pathway utilized by extracellular HSP70: role of toll-like receptor (TLR) 2 and TLR4. J Biol Chem 2002 Apr. 26; 277(17):15028-34.
Brown G D, Gordon S. Immune recognition. A new receptor for beta-glucans. Nature 2001 Sep. 6; 413(6851):36-7.
Bulut Y, Faure E, Thomas L, Karahashi H, Michelsen K S, Equils O, et al. Chlamydial heat shock protein 60 activates macrophages and endothelial cells through Toll-like receptor 4 and MD2 in a MyD88-dependent pathway. J Immunol 2002 Feb. 1; 168(3):1435-40.
Chow J C, Young D W, Golenbock D T, Christ W J, Gusovsky F. Toll-like receptor-4 mediates lipopolysaccharide-induced signal transduction. J Biol Chem 1999 Apr. 16; 274(16):10689-92.
Engering A J, Cella M, Fluitsma D, Brockhaus M, Hoefsmit E C, Lanzavecchia A, et al. The mannose receptor functions as a high capacity and broad specificity antigen receptor in human dendritic cells. Eur J Immunol 1997 September; 27(9):2417-25.
Feinberg H, Mitchell D A, Drickamer K, Weis W I. Structural basis for selective recognition of oligosaccharides by DC-SIGN and DC-SIGNR. Science 2001 Dec. 7; 294 (5549):2163-6.
Frison N, Taylor M E, Soilleux E, Bousser M T, Mayer R, Monsigny M, et al. Oligolysine-based oligosaccharide clusters: selective recognition and endocytosis by the mannose receptor and dendritic cell-specific intercellular adhesion molecule 3 (ICAM-3)-grabbing nonintegrin. J Biol Chem 2003 Jun. 27; 278(26):23922-9.
Hayashi F, Smith K D, Ozinsky A, Hawn T R, Yi E C, Goodlett D R, et al. The innate immune response to bacterial flagellin is mediated by Toll-like receptor 5. Nature 2001 Apr. 26; 410(6832):1099-103.
Heil F, Hemmi H, Hochrein H, Ampenberger F, Kirschning C, Akira S, et al. Species-specific recognition of single-stranded RNA via toll-like receptor 7 and 8. Science 2004 Mar. 5; 303(5663):1526-9.
Hemmi H, Kaisho T, Takeuchi O, Sato S, Sanjo H, Hoshino K, et al. Small anti-viral compounds activate immune cells via the TLR7 MyD88-dependent signaling pathway. Nat Immunol 2002 February; 3(2): 196-200.
Hemmi H, Takeuchi O, Kawai T, Kaisho T, Sato S, Sanjo H, et al. A Toll-like receptor recognizes bacterial DNA. Nature 2000 Dec. 7; 408(6813):740-5.
Kery V, Krepinsky J J, Warren C D, Capek P, Stahl P D. Ligand recognition by purified human mannose receptor. Arch Biochem Biophys 1992 October; 298(1):49-55.
Morr M, Takeuchi O, Akira S, Simon M M, Muhlradt P F. Differential recognition of structural details of bacterial lipopeptides by toll-like receptors. Eur J Immunol 2002 December; 32(12):3337-47.
Okusawa T, Fujita M, Nakamura J, Into T, Yasuda M, Yoshimura A, et al. Relationship between structures and biological activities of mycoplasmal diacylated lipopeptides and their recognition by toll-like receptors 2 and 6. Infect Immun 2004 March; 72(3):1657-65.
Ozinsky A, Underhill D M, Fontenot J D, Hajjar A M, Smith K D, Wilson C B, et al. The repertoire for pattern recognition of pathogens by the innate immune system is defined by cooperation between toll-like receptors. Proc Natl Acad Sci USA 2000 Dec. 5; 97(25):13766-71.
Poltorak A, He X, Smirnova I, Liu M Y, Van Huffel C, Du X, et al. Defective LPS signaling in C3H/HeJ and C57BL/10ScCr mice: mutations in Tlr4 gene. Science 1998 Dec. 11; 282(5396):2085-8.
Schwandner R, Dziarski R, Wesche H, Rothe M, Kirschning C J. Peptidoglycan- and lipoteichoic acid-induced cell activation is mediated by toll-like receptor 2. J Biol Chem 1999 Jun. 18; 274(25):17406-9.
Stambach N S, Taylor M E. Characterization of carbohydrate recognition by langerin, a C-type lectin of Langerhans cells. Glycobiology 2003 May; 13(5):401-10.
Takeuchi O, Kaufmann A, Grote K, Kawai T, Hoshino K, Mon M, et al. Cutting edge: preferentially the R-stereoisomer of the mycoplasmal lipopeptide macrophage-activating lipopeptide-2 activates immune cells through a toll-like receptor 2- and MyD88-dependent signaling pathway. J Immunol 2000 Jan. 15; 164(2):554-7.
Takeuchi O, Sato S, Horiuchi T, Hoshino K, Takeda K, Dong Z, et al. Cutting edge: role of Toll-like receptor 1 in mediating immune response to microbial lipoproteins. J Immunol 2002 Jul. 1; 169(1):10-4.

We claim:

1. An immunogenic composition comprising a complex of a polypeptide antigen and a dendritic cell targeting component, wherein the polypeptide antigen comprises a negatively charged region, wherein the negatively charged region of the polypeptide antigen electrostatically associates with the dendritic cell targeting component, thereby enabling formation of the complex, wherein the dendritic cell targeting component comprises:

or and wherein Pam2Cys refers to dipalmitoyl-S-glycerylcysteine.

2. The immunogenic composition according to claim 1, wherein the polypeptide antigen has an overall negative charge.

3. The immunogenic composition according to claim 1, wherein the polypeptide antigen is associated with the dendritic cell targeting component by electrostatic interaction only.

* * * * *

UNITED STATES PATENT AND TRADEMARK OFFICE
CERTIFICATE OF CORRECTION

PATENT NO. : 9,889,195 B2
APPLICATION NO. : 14/602778
DATED : February 13, 2018
INVENTOR(S) : David Charles Jackson et al.

It is certified that error appears in the above-identified patent and that said Letters Patent is hereby corrected as shown below:

In the Specification

Column 5,
Line 45, "S-[2,3bis(palmitoyloxy)propyl]cysteine" should read --S-[2, 3 bis(palmitoyloxy) propyl] cysteine--.

Column 7,
Line 7, "the -amino" should read --the □-amino--.
Line 46, "subcutaneously" should read --sub-cutaneously--.

Column 12,
Line 59, "Mon M" should read --Morr M--.

Signed and Sealed this
Twenty-seventh Day of November, 2018

Andrei Iancu
*Director of the United States Patent and Trademark Office*